United States Patent
Eda

(10) Patent No.: US 9,427,208 B2
(45) Date of Patent: Aug. 30, 2016

(54) ULTRASONIC OBSERVATION APPARATUS, OPERATION METHOD OF THE SAME, AND COMPUTER READABLE RECORDING MEDIUM

(71) Applicant: OLYMPUS CORPORATION, Tokyo (JP)

(72) Inventor: Hirotaka Eda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/259,350

(22) Filed: Apr. 23, 2014

(65) Prior Publication Data

US 2014/0309531 A1 Oct. 16, 2014

Related U.S. Application Data

(63) Continuation of application No. PCT/JP2013/007565, filed on Sep. 24, 2013.

(30) Foreign Application Priority Data

Oct. 1, 2012 (JP) .................. 2012-219764

(51) Int. Cl.
*A61B 8/00* (2006.01)
*A61B 8/14* (2006.01)
(Continued)

(52) U.S. Cl.
CPC ............ *A61B 8/14* (2013.01); *A61B 8/469* (2013.01); *A61B 8/485* (2013.01); *A61B 8/5207* (2013.01);
(Continued)

(58) Field of Classification Search
CPC ...... A61B 8/469; A61B 8/5207; A61B 8/54; A61B 8/14; A61B 8/463
See application file for complete search history.

(56) References Cited

U.S. PATENT DOCUMENTS 5,301,674 A * 4/1994 Erikson et al. ............... 600/447
6,217,516 B1 * 4/2001 Poland et al. ................ 600/437
(Continued)

FOREIGN PATENT DOCUMENTS

| EP | 2 599 440 | 6/2013 |
|----|-----------|--------|
| JP | 3-73135 A | 3/1991 |

(Continued)

OTHER PUBLICATIONS

International Search Report dated Jan. 7, 2014 from related International Application No. PCT/JP2013/075765.
(Continued)

*Primary Examiner* — Amanda Lauritzen Moher
(74) *Attorney, Agent, or Firm* — Scully, Scott, Murphy & Presser, P.C.

(57) ABSTRACT

An ultrasonic observation apparatus includes: a region of interest setting unit capable of setting information on a region of interest; a focus point calculation unit that divides the region of interest into a plurality of partial regions of interest according to the number of focus points in the region of interest, calculates a focus point in each of the partial regions of interest, and determines a transmission timing according to calculation results; a transmitting and receiving unit that performs a transmission-and-reception of an ultrasonic wave which is focused on the focus point; a frequency analysis unit that calculates a plurality of frequency spectra by analyzing the received ultrasonic wave with reference to the focus point; a feature data extracting unit that approximates the frequency spectra to extract feature data thereof; and an image processing unit that generates display image data based on the feature data. The focus point calculation unit does not set a focus point according to the number of focus points in the partial regions of interest including the focus point for the B-mode image.

7 Claims, 15 Drawing Sheets

(51) Int. Cl.
*A61B 8/08* (2006.01)
*G01S 7/52* (2006.01)

(52) U.S. Cl.
CPC .............. *A61B 8/5246* (2013.01); *A61B 8/54* (2013.01); *G01S 7/5202* (2013.01); *G01S 7/52033* (2013.01); *G01S 7/52036* (2013.01); *A61B 8/0858* (2013.01); *A61B 8/4461* (2013.01); *A61B 8/463* (2013.01); *A61B 8/5269* (2013.01); *G01S 7/52073* (2013.01); *G01S 7/52074* (2013.01)

(56) References Cited

U.S. PATENT DOCUMENTS

| | | | |
|---|---|---|---|
| 8,002,705 | B1 | 8/2011 | Napolitano et al. |
| 8,192,362 | B2 * | 6/2012 | Kolios et al. ............ 600/438 |
| 2004/0087856 | A1 * | 5/2004 | Panda et al. ............ 600/443 |
| 2005/0154306 | A1 * | 7/2005 | Burcher et al. .......... 600/447 |
| 2007/0239014 | A1 | 10/2007 | Yoshikawa et al. |
| 2008/0051659 | A1 | 2/2008 | Waki et al. |
| 2012/0215110 | A1 | 8/2012 | Wilkening et al. |
| 2013/0011038 | A1 | 1/2013 | Eda |

FOREIGN PATENT DOCUMENTS

| | | |
|---|---|---|
| JP | 7-323029 A | 12/1995 |
| JP | 2004-321582 A | 11/2004 |
| JP | 2005-245788 A | 9/2005 |
| JP | 2012-157387 A | 8/2012 |
| WO | 93/19673 A1 | 10/1993 |
| WO | 2005/122906 A1 | 12/2005 |
| WO | 2012/063928 A1 | 5/2012 |
| WO | 2012/063977 A1 | 5/2012 |

OTHER PUBLICATIONS

Extended Supplementary European Search Report dated Apr. 19, 2016 in European Application No. 13 84 3757.9.

* cited by examiner

FIG.4

| SIZE OF REGION OF INTEREST IN DEPTH DIRECTION w (cm) | NUMBER OF FOCUS POINTS |
|---|---|
| 1 | 1 |
| 2 | 1 |
| 3 | 2 |
| 4 | 3 |
| 5 | 3 | ic wave along a sound ray in the region of interest as many
ULTRASONIC OBSERVATION APPARATUS, OPERATION METHOD OF THE SAME, AND COMPUTER READABLE RECORDING MEDIUM

CROSS REFERENCES TO RELATED APPLICATIONS

This application is a continuation of PCT international application Ser. No. PCT/JP2013/075765 filed on Sep. 24, 2013 which designates the United States, incorporated herein by reference, and which claims the benefit of priority from Japanese Patent Application No. 2012-219764, filed on Oct. 1, 2012, incorporated herein by reference.

BACKGROUND OF THE INVENTION

1. Field of the Invention

The present invention relates to an ultrasonic observation apparatus, an operation method of the ultrasonic observation apparatus, and a computer readable recording medium, for observing tissue of a specimen by using ultrasonic waves.

2. Description of the Related Art

Conventionally, as an examination technique for breast cancer or the like using ultrasonic waves, a technique called ultrasonic elastography has been known (for example, see International Patent Publication No. WO2005/122906). Ultrasonic elastography is a technique of applying the fact that hardness of cancers and tumor tissue differs according to progress of the diseases and the organisms. In this technique, while a location to be examined is pressed from outside, a strain and an elastic modulus of biological tissue at that location to be examined are measured by using ultrasonic waves, and results of this measurement is image-displayed as tomographic images.

SUMMARY OF THE INVENTION

An ultrasonic observation apparatus according to the invention is an ultrasonic observation apparatus that transmits an ultrasonic wave to a specimen and receives the ultrasonic wave reflected from the specimen. The ultrasonic observation apparatus includes: a region of interest setting unit that is able to set information on a position, and a length in a depth direction, of a region of interest in the specimen; a focus point calculation unit that divides the region of interest into a plurality of partial regions of interest according to the number of focus points in the region of interest, the number of focus points being a parameter associated with the length of the region of interest set by the region of interest setting unit, calculates a focus point in each of the partial regions of interest, and determines a transmission timing according to the calculated focus point; a transmitting and receiving unit that performs a transmission-and-reception of an ultrasonic wave along a sound ray in the region of interest as many times as the number of focus points along the sound ray, the transmission-and-reception of the ultrasonic wave being focused on the focus point calculated by the focus point calculation unit; a frequency analysis unit that calculates a plurality of frequency spectra by analyzing the ultrasonic wave received by the transmitting and receiving unit with reference to the focus point; a feature data extracting unit that extracts feature data of the frequency spectra calculated by the frequency analysis unit by approximating the frequency spectra; and an image processing unit that generates display image data based on the feature data extracted by the feature data extracting unit. The focus point calculation unit sets a focus point for a B-mode image for displaying brightness converted from amplitude of the ultrasonic wave reflected from the specimen, and does not set a focus point according to the number of focus points in the partial regions of interest including the focus point for the B-mode image.

An operation method of an ultrasonic observation apparatus according to the invention is an operation method of an ultrasonic observation apparatus that transmits an ultrasonic wave to a specimen and receives the ultrasonic wave reflected from the specimen. The operation method includes: setting a position, and a length in a depth direction, of a region of interest in the specimen; dividing the region of interest into a plurality of partial regions of interest according to the number of focus points in the region of interest, the number of focus points being a parameter associated with the length of the region of interest, and calculating a focus point in each of the partial regions of interest; determining a transmission timing according to the focus point; performing a transmission-and-reception of an ultrasonic wave along a sound ray in the region of interest as many times as the number of focus points on the sound ray, the transmission-and-reception of the ultrasonic wave being focused on the focus point; calculating a plurality of frequency spectra by analyzing a received ultrasonic wave with reference to the focus point; extracting feature data of the frequency spectra by approximating the frequency spectra; and generating display image data based on the feature data. The calculating of the focus point includes setting a focus point for a B-mode image for displaying brightness converted from amplitude of the ultrasonic wave reflected from the specimen and not setting a focus point according to the number of focus points in the partial regions of interest including the focus point for the B-mode image.

A non-transitory computer readable recording medium according to the invention is a non-transitory computer readable recording medium having an executable program recorded thereon. The program instructs a processor to execute: setting a position, and a length in a depth direction, of a region of interest in the specimen; dividing the region of interest into a plurality of partial regions of interest according to the number of focus points in the region of interest, the number of focus points being a parameter associated with the length of the region of interest, and calculating a focus point in each of the partial regions of interest; determining a transmission timing according to the focus point; performing a transmission-and-reception of an ultrasonic wave along a sound ray in the region of interest as many times as the number of focus points on the sound ray, the transmission-and-reception of the ultrasonic wave being focused on the focus point; calculating a plurality of frequency spectra by analyzing a received ultrasonic wave with reference to the focus point; extracting feature data of the frequency spectra by approximating the frequency spectra; and generating ultrasonic image data having a display mode corresponding to the feature data. The calculating of the focus point includes setting a focus point for a B-mode image for displaying brightness converted from amplitude of the ultrasonic wave reflected from the specimen and not setting a focus point according to the number of focus points in the partial regions of interest including the focus point for the B-mode image.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 4 is a diagram illustrating a focus point information table stored by a focus point information storage unit;

DETAILED DESCRIPTION OF THE PREFERRED EMBODIMENTS

Hereinafter, with reference to the appended drawings, modes for carrying out the present invention (hereinafter, referred to as "embodiments") will be described.

First Embodiment

Figure 1:
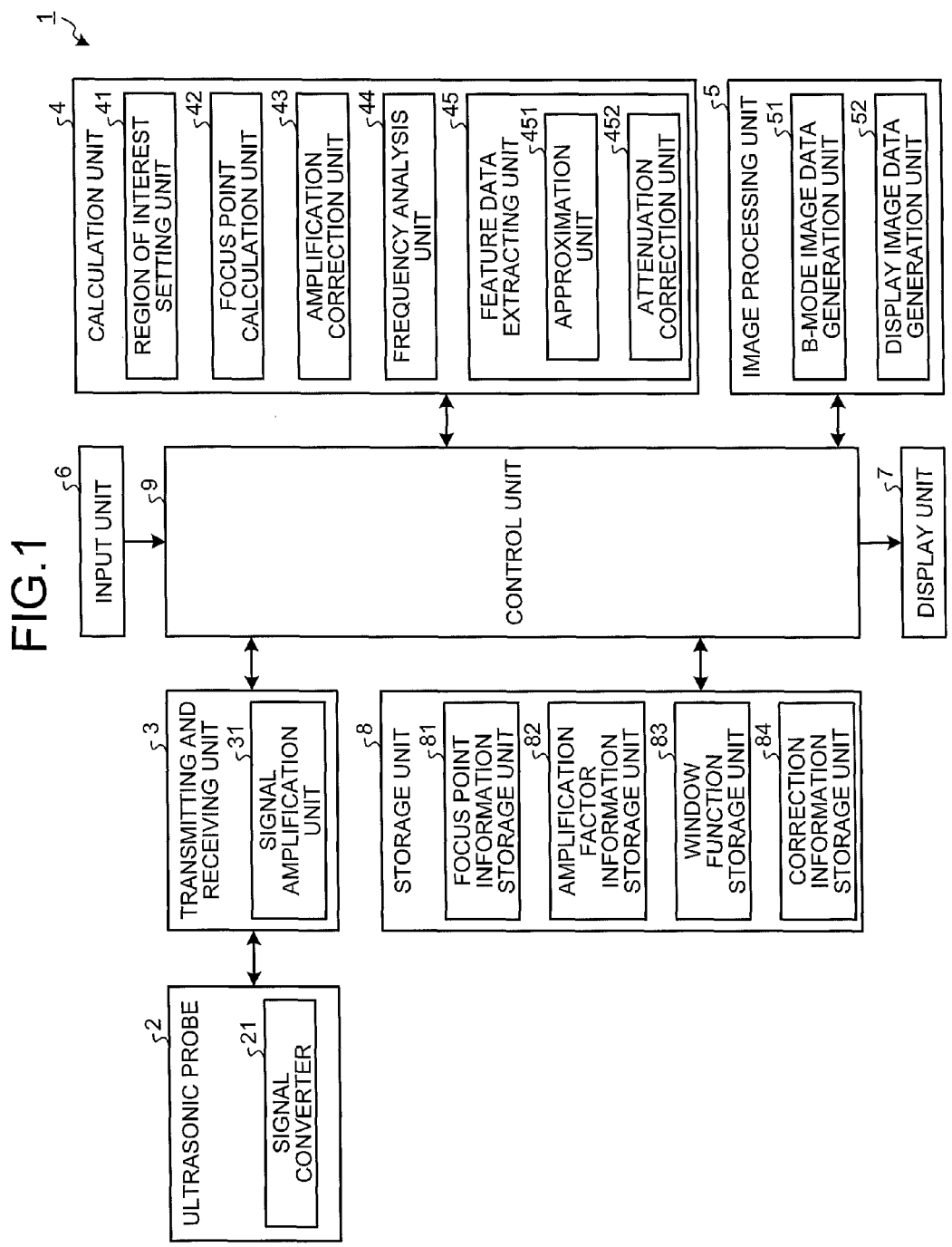
FIG. 1 is a block diagram illustrating a configuration of an ultrasonic observation apparatus according to a first embodiment of the present invention.

FIG. 1 is a block diagram illustrating a configuration of an ultrasonic observation apparatus according to a first embodiment of the present invention. An ultrasonic observation apparatus 1 illustrated in the figure is an apparatus for observing a specimen to be diagnosed, by using ultrasonic waves.

The ultrasonic observation apparatus 1 includes: an ultrasonic probe 2 that outputs an ultrasonic pulse to outside thereof and receives an ultrasonic echo reflected outside thereof; a transmitting and receiving unit 3 that performs transmission and reception of an electric signal to and from the ultrasonic probe 2; a calculation unit 4 that performs specified calculation on an electric echo signal converted from the ultrasonic echo; an image processing unit 5 that performs generation of image data corresponding to the electric echo signal converted from the ultrasonic echo; an input unit 6 that is realized by using an interface, such as a key board, a mouse, a touch panel, or the like, and receives input of various information; a display unit 7 that is realized by using a display panel made of a liquid crystal, an organic EL, or the like, and displays various information including an image generated by the image processing unit 5; a storage unit 8 that stores various types of information including information on tissue characterization of a known specimen; and a control unit 9 that performs operation control of the ultrasonic observation apparatus 1.

The ultrasonic probe 2 has a signal converter 21 that converts an electric pulse signal received from the transmitting and receiving unit 3 into an ultrasonic pulse (sound pulse signal) and converts an ultrasonic echo reflected from a specimen outside thereof into an electric echo signal. The ultrasonic probe 2 may cause an ultrasonic transducer to mechanically perform scanning or may cause a plurality of ultrasonic transducers to electronically perform scanning.

The transmitting and receiving unit 3 is electrically connected to the ultrasonic probe 2, transmits a pulse signal to the ultrasonic probe 2, and receives an echo signal, which is a received signal, from the ultrasonic probe 2. The received echo signal is for switching over between: an echo signal (hereinafter, referred to as "B-mode image echo signal") used by the image processing unit 5 in order to generate B-mode image data by converting amplitude of an echo signal to brightness; and an echo signal (hereinafter, referred to as "calculation echo signal") used by the calculation unit 4 in order to perform calculation. The switch-over between the transmission of the pulse signal to acquire the B-mode image echo signal and the transmission of the pulse signal to acquire the calculation echo signal is performed, under the control of the control unit 9, frame by frame or sound ray by sound ray.

The transmitting and receiving unit 3 generates a pulse signal, based on a focus point and a transmission timing set by a later described focus point calculation unit 42 and a preset waveform, transmits this generated pulse signal to the ultrasonic probe 2, performs processes, such as amplification and filtering, on the echo signal received by the ultrasonic probe 2, and thereafter, by performing A/D conversion, generates digital RF signals of the B-mode image echo signal and calculation echo signal. If the ultrasonic probe 2 is to cause a plurality of ultrasonic transducers to electronically perform scanning, the transmitting and receiving unit 3 has a multi-channel circuit for beam combination corresponding to the plurality of ultrasonic wave sound wave generators.

Figure 2:
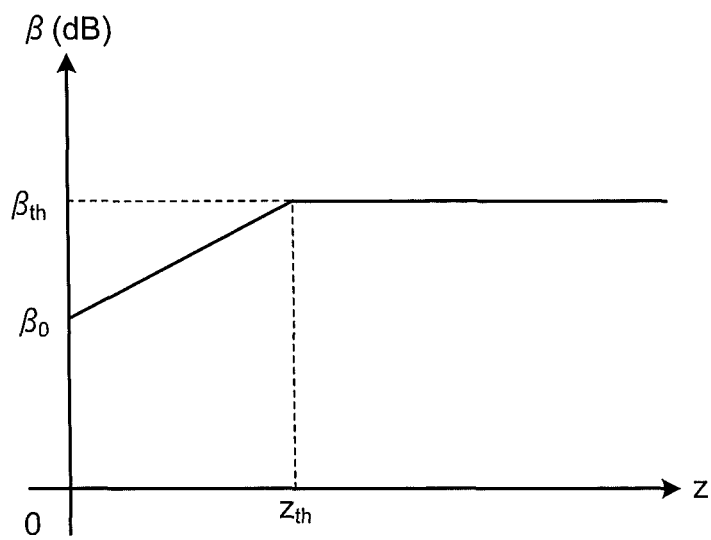
FIG. 2 is a diagram illustrating a relation between receiving depth and amplification factor of an echo signal.

The transmitting and receiving unit 3 has a signal amplification unit 31 that amplifies an echo signal. Specifically, the signal amplification unit 31 performs sensitivity time control (STC) correction that amplifies an echo signal with a larger receiving depth with a higher amplification factor. FIG. 2 is a diagram illustrating a relation between receiving depth and amplification factor of an echo signal. Receiving depth "z" illustrated in FIG. 2 is quantity calculated based on elapsed time from a time point at which ultrasonic reception starts. As illustrated in FIG. 2, amplification factor β (dB) linearly increases from $\beta_0$ to $\beta_{th}$ (>$\beta_0$) as the receiving depth "z" increases, if the receiving depth "z" is less than a threshold value $z_{th}$. Further, the amplification factor β takes a constant value $\beta_{th}$ if the receiving depth "z" is equal to or greater than the threshold value $z_{th}$. The threshold value $z_{th}$ is a value at which an ultrasonic signal received from the specimen has almost attenuated and noises have become dominant. In more general, if the receiving depth "z" is less than the threshold value $z_{th}$, the amplification factor β monotonically increases as the receiving depth "z" increases.

The calculation unit 4 includes: a region of interest setting unit 41 that sets, according to input by the input unit 6, information on a position and a size of a region of interest (ROI); a focus point calculation unit 42 that sets a transmission timing; an amplification correction unit 43 that performs amplification correction of making amplification factor constant regardless of receiving depth for a digital RF signal output by the transmitting and receiving unit 3; a frequency analysis unit 44 that performs frequency analysis of an echo signal by performing fast Fourier transform (FFT) on a digital RF signal of a calculation echo signal output by the transmitting and receiving unit 3; and a feature data extracting unit 45 that extracts, by approximating a frequency spectrum (power spectrum) acquired by the frequency analysis performed by the frequency analysis unit 44, feature data of the frequency spectrum.

The region of interest setting unit 41 sets a region of interest, based on information on a length of a region of interest in a depth direction, a position of the region of interest and the number of sound rays, the information being specified and input by the input unit 6.

The focus point calculation unit 42 performs calculation (position setting) of a plurality of focus points in the region of interest, from the information on the size of the region of interest set by the region of interest setting unit 41 and a table of the numbers of focus points stored by a focus point information storage unit 81 (later described), which the storage unit 8. In order to generate a digital RF signal (received signal) of the calculation echo signal (received signal) per sound ray, the focus point calculation unit 42 determines the number of transmissions and a timing of an electric pulse signal for transmitting from the transmitting and receiving unit 3 to the ultrasonic probe 2 to converge the ultrasonic wave at the focus point at the time of transmission. Further, the focus point calculation unit 42 determines a focus point of the B-mode image echo signal, the number of transmissions, and a timing of an electric pulse signal for transmitting from the transmitting and receiving unit 3 to the ultrasonic probe 2 to converge the ultrasonic wave at the focus point at the time of transmission.

Figure 3:
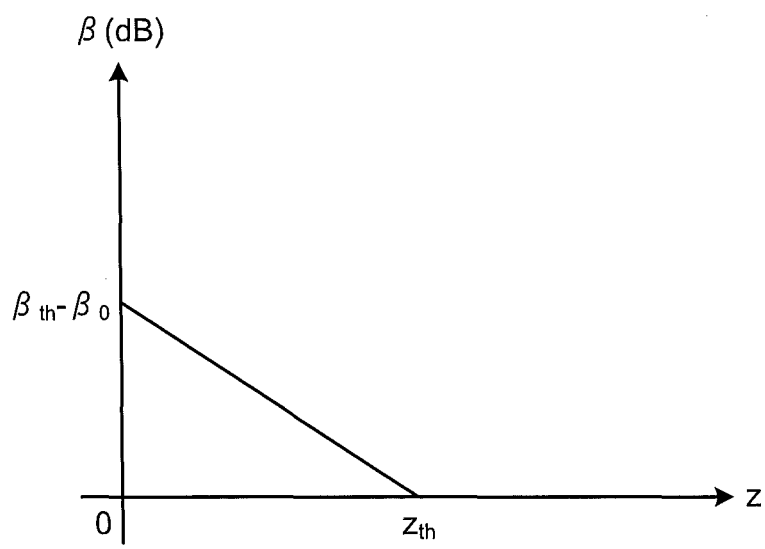
FIG. 3 is a diagram illustrating a relation between receiving depth and amplification factor in an amplification process performed by an amplification correction unit.

FIG. 3 is a diagram illustrating a relation between receiving depth and amplification factor in an amplification process performed by the amplification correction unit 43. As illustrated in FIG. 3, the amplification factor β(dB) in the amplification process performed by the amplification correction unit 43 takes the maximum value $\beta_{th}$-$\beta_0$ when the receiving depth "z" is zero, linearly decreases until the receiving depth "z" reaches the threshold value $z_{th}$ from zero, and is zero when the receiving depth "z" is equal to or greater than the threshold value $z_{th}$. By the amplification correction unit 43 performing the amplification correction on the digital RF signal with the amplification factor determined as described above, influence of STC correction in the signal amplification unit 31 is able to be offset and a signal of a constant amplification factor $\beta_{th}$ is able to be output. Of course, the relation between the receiving depth "z" and the amplification factor β used by the amplification correction unit 43 differs according to the relation between the receiving depth and the amplification factor in the signal amplification unit 31.

The frequency analysis unit 44 calculates frequency spectra at a plurality of locations (data positions) on a sound ray, by performing fast Fourier transform on an FFT data group formed of a specified data amount, for each sound ray. Frequency spectra demonstrate different trends according to tissue characterization of the specimen. This is because, a frequency spectrum has a correlation with size, density, sound impedance, and the like of the specimen as a scatterer that scatters ultrasonic waves. "Tissue characterization" herein is any of, for example, cancer, endocrine tumor, mucinous tumor, pancreatitis, vessel, and the like.

The feature data extracting unit 45 extracts, by approximating a frequency spectrum of each data position calculated by the frequency analysis unit 44, feature data of that frequency spectrum. The feature data extracting unit 45 has: an approximation unit 451 that calculates, by performing an approximation process on the frequency spectrum calculated by the frequency analysis unit 44, pre-correction feature data before being subjected to an attenuation correction process; and an attenuation correction unit 452 that extracts feature data by performing the attenuation correction process on the pre-correction feature data approximated by the approximation unit 451.

The approximation unit 451 approximates the frequency spectrum with a linear equation by regression analysis and extracts pre-correction feature data that characterize this approximated linear equation. Specifically, the approximation unit 451 calculates a gradient $a_0$ and an intercept $b_0$ of the linear equation by regression analysis and calculates, as the pre-correction feature data, intensity at a particular frequency within a frequency band in the frequency spectrum. In this first embodiment, the approximation unit 451 uses a mid-frequency $f_{MID}=(f_{Low}+f_{HIGH})/2$ as the particular frequency and calculates an intensity (mid-band fit) $c_0=a_0 f_{MID}+b_0$ at this mid-frequency $f_{MID}$, but that is just an example. The "intensity" referred to herein means any of parameters such as voltage, electric power, sound pressure, and sound energy.

Of the three feature data, the gradient $a_0$ has a correlation with a size of a scatterer of ultrasonic waves and in general, is considered to have a smaller value as the scatterer becomes larger. Further, the intercept $b_0$ has a correlation with the size of the scatterer, a difference in sound impedances, a density (concentration) of the scatterer, and the like. Specifically, the intercept $b_0$ is considered to have a larger value as the scatterer becomes larger, have a larger value as the sound impedance becomes greater, and have a larger value as the density (concentration) of the scatterer becomes larger. The intensity $c_0$ at the mid-frequency $f_{MID}$ (hereinafter, simply referred to as "intensity") is an indirect parameter derived from the gradient $a_0$ and the intercept $b_0$ and gives a spectrum intensity at the center of an effective frequency band. Therefore, the intensity $c_0$ is considered to have a certain degree of correlation with brightness of a B-mode image, in addition to the size of the scatterer, the difference between the sound impedances, and the density of the scatterer. The approximation equation calculated by the approximation unit 451 is not limited to a linear equation and may be a polynomial equation of the second or higher order.

Next, correction performed by the attenuation correction unit 452 will be described. In general, an attenuation amount "A" of a sound wave is able to be expressed by the following.

$$A = 2\alpha z f \quad (1)$$

Here, $\alpha$ is an attenuation factor and "z" is the receiving depth of an ultrasonic wave, and "f" is frequency. As is clear from equation (1), the attenuation amount "A" is proportional to the frequency "f". A specific value of the attenuation factor $\alpha$ is, for an organism, 0 to 1.0 (dB/cm/MHz), and more preferably, is 0.3 to 0.7 (dB/cm/MHz), and is determined according to a type of an organ to be observed. In the first embodiment, a configuration that allows the value of the attenuation factor $\alpha$ to be changed by input from the input unit 6 may be used.

The attenuation correction unit 452 corrects the pre-correction feature data (gradient $a_0$, intercept $b_0$, intensity $c_0$) extracted by the approximation unit 451, as follows.

$$a = a_0 + 2\alpha z \quad (2)$$

$$b = b_0 \quad (3)$$

$$c = c_0 + 2\alpha z f_{MID} (= a f_{MID} + b) \quad (4)$$

As is clear from Equations (2) and (4), the attenuation correction unit 452 performs correction of a larger correction amount as the receiving depth "z" of the ultrasonic wave increases. Further, according to Equation (3), the correction related to the intercept is identical transformation. This is because, the intercept is a frequency component corresponding to a frequency of 0 (Hz) and does not attenuate.

The image processing unit 5 generates display image data based on the feature data extracted by the feature data extracting unit 45. The image processing unit 5 has: a B-mode image data generation unit 51 that generates B-mode image data for displaying brightness converted from amplitude of a B-mode image echo signal; and a display image data generation unit 52 that generates display image data by using data respectively output by the B-mode image data generation unit 51 and the calculation unit 4.

The B-mode image data generation unit 51 generates the B-mode image data by performing signal processing using a known technique such as a band pass filter, logarithmic transformation, gain processing, contrast processing, or the like on a digital signal and by performing decimation or the like of data according to a step width of the data determined according to an image display range in the display unit 7.

The display image data generation unit 52 generates display image data including tissue characterization highlighted image that highlights tissue characterization of a subject, by using the B-mode image data generated by the B-mode image data generation unit 51 and the feature data calculated by the feature data extracting unit 45.

The input unit 6 is realized by using the interface such as the key board, mouse, touch panel, or the like. The input unit 6 receives input of information specifying the region of interest by a user of the ultrasonic observation apparatus 1, who has seen an image generated by the image processing unit 5.

The storage unit 8 includes: a focus point information storage unit 81 that stores the number of focus points and a length in a depth direction in a region of interest in association with each other; an amplification factor information storage unit 82 that that stores information of an amplification factor that the signal amplification unit 31 and the amplification correction unit 43 refer to when an amplification process is performed; a window function storage unit 83 that stores a window function used upon a frequency analysis process performed by the frequency analysis unit 44; and a correction information storage unit 84 that stores correction information that the attenuation correction unit 452 refers to when the attenuation correction unit 452 performs a process.

The focus point information storage unit 81 stores the number of focus points, and the size of the region of interest in the depth direction which is size information of the region of interest, in association with each other. FIG. 4 is a diagram illustrating a focus point information table stored by the focus point information storage unit 81. In a focus point information table Tb illustrated in this figure, as a size "w" of the region of interest in the depth direction becomes greater, the number of focus points increases stepwisely. Specifically, when w=1 or 2 (cm), the number of focus points is one, when w=3 (cm), the number of focus points is two, and when w=4 or 5 (cm), the number of focus points is three. The number of focus points corresponds to the number of region divisions in the region of interest and also corresponds to the number of ultrasonic transmissions per sound ray.

The amplification factor information storage unit 82 stores the relation between the amplification factor and receiving depth illustrated in FIGS. 2 and 3.

The window function storage unit 83 stores at least any one window function or a plurality of window functions of Hamming, Hanning, and Blackman window functions and the like.

The correction information storage unit 84 stores information on attenuation correction including Equations (2) to (4).

The storage unit 8 is realized by using a ROM, in which an operation program of the ultrasonic observation apparatus 1, a program that activates a specified OS and the like are stored beforehand, a RAM that stores calculation parameters and data of each processes, and the like.

The control unit 9 is realized by using a CPU that has calculating and controlling functions. The control unit 9 executes various calculation processes related to an operation method of the ultrasonic observation apparatus 1 by reading from the storage unit 8 information and various programs including the operation program of the ultrasonic observation apparatus 1 stored by the storage unit 8 to thereby comprehensively control the ultrasonic observation apparatus 1.

Structural elements other than the transducer 2 of the ultrasonic observation apparatus 1 having the above described functions and configuration is realized by using one computer or a plurality of computers.

The operation program of the ultrasonic observation apparatus 1 may be recorded in a computer readable recording medium, such as a hard disk, a flash memory, a CD-ROM, a DVD-ROM, or a flexible disk, and widely distributed.

Figure 5:
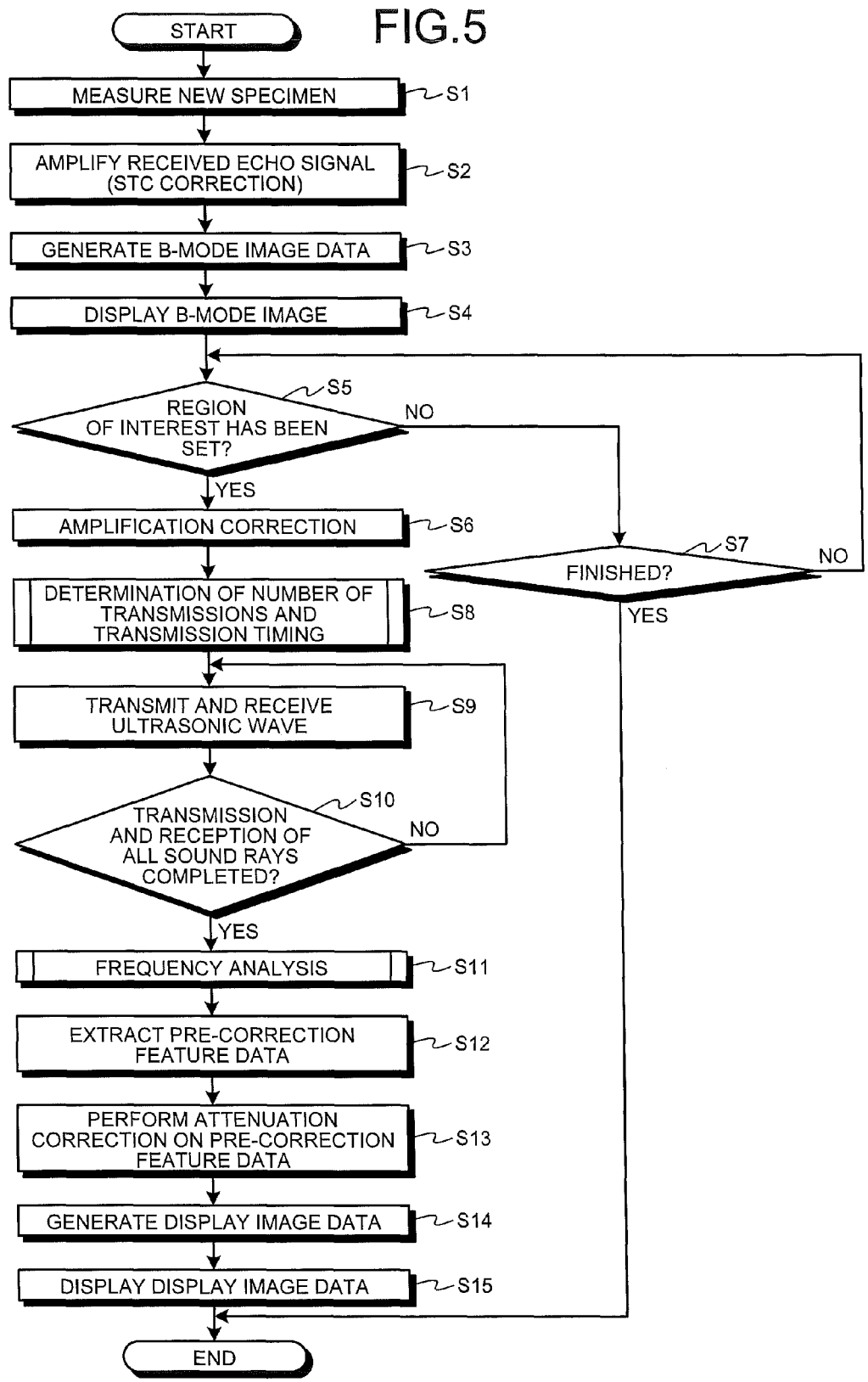
FIG. 5 is a flow chart illustrating an outline of a process of the ultrasonic observation apparatus according to the first embodiment of the present invention.

FIG. 5 is a flow chart illustrating an outline of a process of the ultrasonic observation apparatus 1 having the above described configuration. In FIG. 5, the ultrasonic observation apparatus 1 performs measurement of a new specimen by using the ultrasonic probe 2 (step S1).

Subsequently, the signal amplification unit 31 that has received an echo signal from the ultrasonic probe 2 performs amplification of that echo signal (step S2). The signal amplification unit 31 performs the amplification based on the relation between the amplification factor and the receiving depth illustrated in FIG. 2.

Thereafter, the B-mode image data generation unit 51 generates B-mode image data by using a B-mode image echo signal output by the transmitting and receiving unit 3 (step S3).

Figure 6:
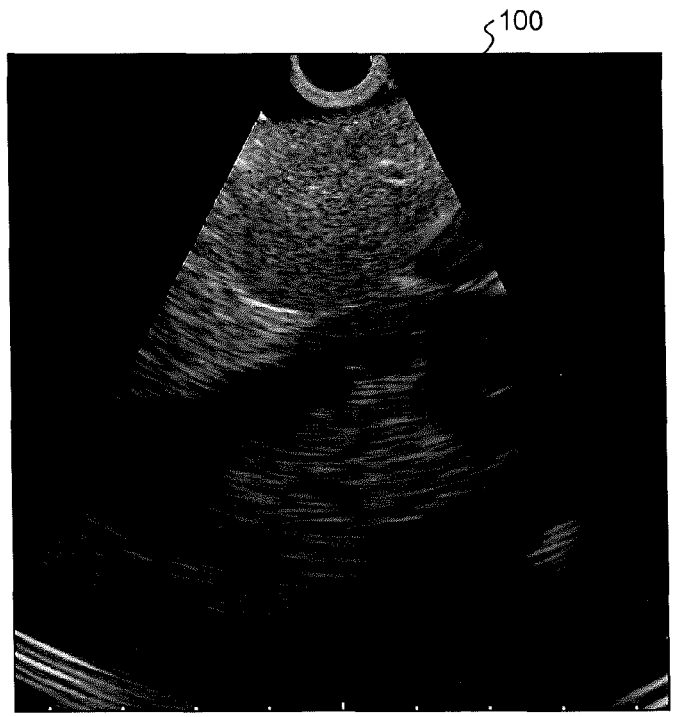
FIG. 6 is a diagram illustrating a display example of a B-mode image in a display unit.

Subsequently, the control unit 9 performs control to cause the display unit 7 to display a B-mode image corresponding to the B-mode image data generated by the B-mode image data generation unit 51 (step S4). FIG. 6 is a diagram illustrating a display example of the B-mode image in the display unit 7. A B-mode image 100 illustrated in this figure is a gray scale image in which values of red (R), green (G), and blue (B), which are variables when an RGB color system is used as a color space, are matched with one another.

Thereafter, if the region of interest setting unit 41 sets a region of interest according to input by the input unit 6 (step S5: Yes), the amplification correction unit 43 performs, on a signal output from the transmitting and receiving unit 3, correction such that the amplification factor becomes constant regardless of the receiving depth (step S6). The amplification correction unit 43 performs an amplification process based on the relation between the amplification factor and receiving depth illustrated in FIG. 3. The region of interest in the B-mode image may be arbitrarily set by a user via the input unit 6.

If the region of interest is not set by the region of interest setting unit 41 in step S5 (step S5: No) and an instruction to end the process is input by the input unit 6 (step S7, Yes), the ultrasonic observation apparatus 1 ends the process. In contrast, if the region of interest has not been set (step S5: No) and the instruction to end the process has not been input by the input unit 6 (step S7: No), the ultrasonic observation apparatus 1 returns to step S5.

Figure 7:
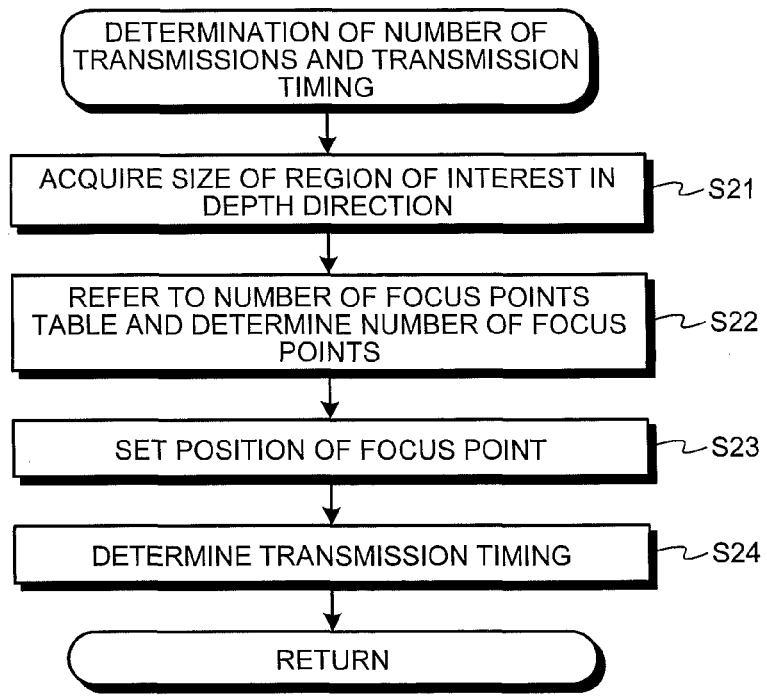
FIG. 7 is a flow chart illustrating an outline of a process performed by a focus point calculation unit.

Subsequently, in order to acquire a calculation echo signal (received signal), the focus point calculation unit 42 determines the number of transmissions and a timing of an electric pulse signal for transmitting from the transmitting and receiving unit 3 to the ultrasonic probe 2 to converge the ultrasonic wave at the focus point at the time of transmission (step S8). FIG. 7 is a flow chart illustrating an outline of a process of determining the number of transmissions and timing of the electric pulse signal for transmitting from the transmitting and receiving unit 3 to the ultrasonic probe 2 to converge the ultrasonic wave at the focus point at the time of transmission, performed by the focus point calculation unit 42. First, the focus point calculation unit 42 acquires a length in a depth direction of the region of interest specified in step S5 (step S21).

Thereafter, the focus point calculation unit 42 refers to a focus point number table stored in the storage unit 8 and determines the number of focus points (the number of transmissions) corresponding to the acquired size of the region of interest in the depth direction (step S22).

Subsequently, the focus point calculation unit 42 divides the region of interest into the determined number of focus points in the depth direction, and sets a central position in the depth direction in each divided partial region of interest as a focus point (step S23). At step S23, the focus point calculation unit 42 may calculate, as the focus point, a central data position of a data array in the depth direction in each partial region of interest.

Lastly, the focus point calculation unit 42 determines a transmission timing such that an ultrasonic wave is focused to the position of each set focus point (step S24).

As described above, the focus point calculation unit 42 determines the number of transmissions and transmission timing for acquiring an echo signal. Thereafter, the ultrasonic observation apparatus 1 returns to a main routine illustrated in FIG. 5.

Subsequently to the above described step S8, the transmitting and receiving unit 3 transmits a pulse signal that has been set beforehand to the ultrasonic probe 2 at the determined transmission timing and receives a calculation echo signal, which is a received signal from the ultrasonic probe 2 (step S9).

Figure 8:
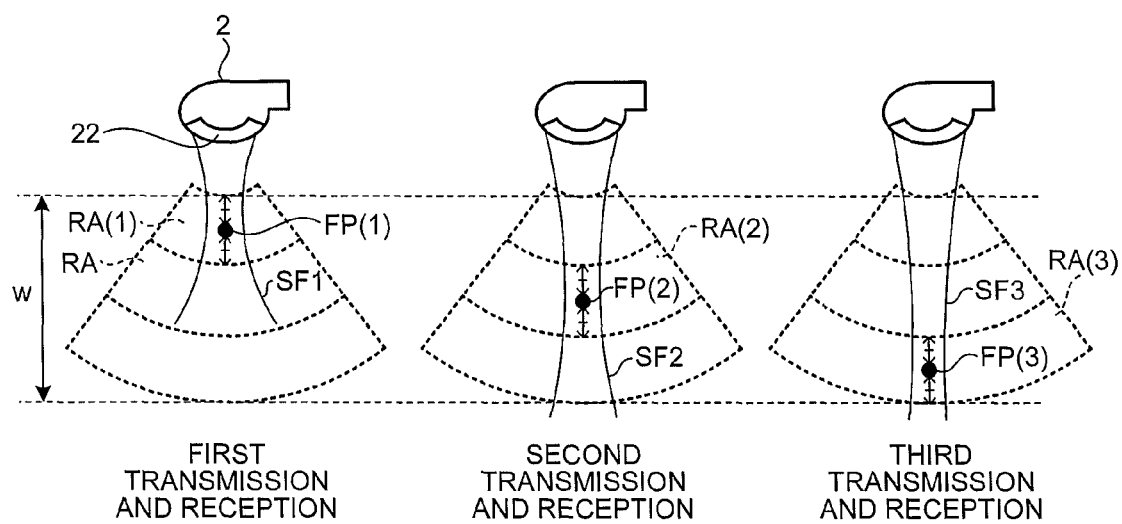
FIG. 8 is a diagram schematically illustrating an outline of an ultrasonic transmission process performed by an ultrasonic probe.

FIG. 8 is a diagram schematically illustrating an outline of an ultrasonic transmission process performed by the ultrasonic probe 2. In FIG. 8, a case in which a size "w" of a region of interest in a depth direction is 4 cm is illustrated. In this case, if a relation between "w" and the number of focus points follows the focus point information table Tb illustrated in FIG. 4, the number of focus points is three. Therefore, a region of interest RA is divided into three partial regions of interest RA(1), RA(2), and RA(3), and to a partial region of interest RA(j)(j=1, 2, 3), a focus point FP(j) is set (see the above described step S23).

In the case illustrated in FIG. 8, an ultrasonic transducer 22 of the ultrasonic probe 2 sequentially transmits, along one sound ray, three ultrasonic waves at specified transmission timing and receives a calculation echo signal, the three ultrasonic waves forming sound fields having the three focus points respectively set in the partial regions of interest at their centers. Specifically, in a first transmission and reception, the ultrasonic transducer 22 forms a sound field SF1 approximately symmetrical in a travelling direction of the ultrasonic wave with a focus point FP(1) at its center. Further, in a second transmission and reception, the ultrasonic transducer 22 forms a sound field SF2 approximately symmetrical in the travelling direction of the ultrasonic wave with a focus point FP(2) at its center. Furthermore, in a third transmission and reception, the ultrasonic transducer 22 forms a sound field SF3 approximately symmetrical in the travelling direction of the ultrasonic wave with a focus point FP(3) at its center. In FIG. 8, although one sound ray at the center of the region of interest RA is exemplified, actually, for every sound ray included in the region of interest RA, a process similar to that described above (ultrasonic transmission and reception) is of course performed.

Figure 9:
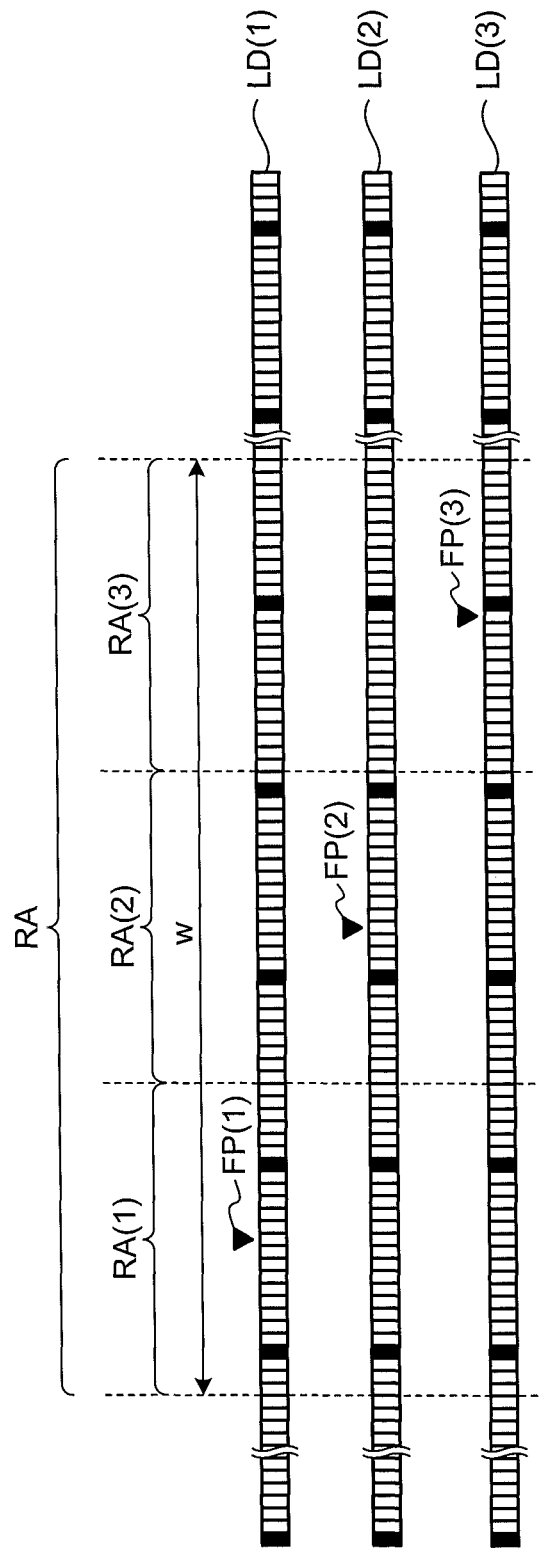
FIG. 9 is a diagram schematically illustrating a configuration of a calculation echo signal per sound ray received by a transmitting and receiving unit from the ultrasonic probe.

FIG. 9 is a diagram schematically illustrating a configuration of calculation echo signals per sound ray received from the ultrasonic probe 2 by the transmitting and receiving unit 3 in step S9. Sound rays LD(1) to LD(3) illustrated the figure are calculation echo signals respectively received by the transmitting and receiving unit 3 in the first transmission and reception to third transmission and reception, and a white or black rectangle in each signal means one data. Further, the sound rays LD(1) to LD(3) are discretized at time intervals corresponding to a sampling frequency (for example, 50 MHz) in A/D conversion performed by the transmitting and receiving unit 3. The black rectangle illustrated in FIG. 9 means a data position representing an FFT data group acquired by the frequency analysis unit 44. This point will be described in detail with reference to later described step S11.

Thereafter, if ultrasonic transmissions and receptions of a specified number of transmissions for every sound ray have been completed (step S10: Yes), the frequency analysis unit 44 performs frequency analysis of the calculation echo signals (step S11). In contrast, if the ultrasonic transmissions and receptions of the specified number of transmissions for every sound ray have not been completed (step S10: No), the ultrasonic observation apparatus 1 returns to step S9.

Figure 10:
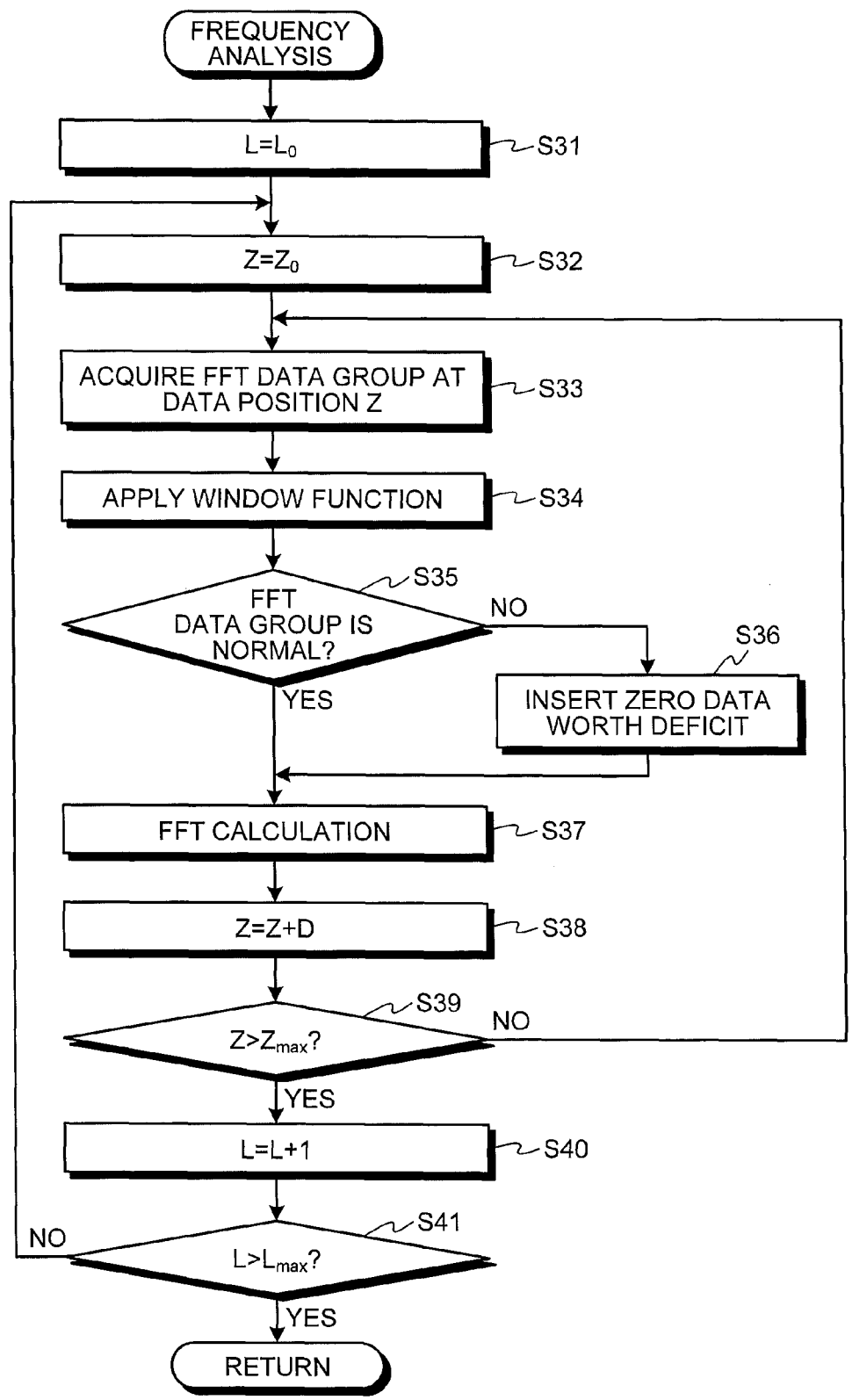
FIG. 10 is a flow chart illustrating an outline of a process performed by a frequency analysis unit.

A process (step S11) performed by the frequency analysis unit 44 will now be described in detail with reference to a flow chart illustrated in FIG. 10. First, the frequency analysis unit 44 sets a sound ray number "L" of a sound ray to be analyzed first as an initial value $L_0$ (step S31). The initial value $L_0$ may be given to a sound ray first received by the transmitting and receiving unit 3, or given to a sound ray corresponding to one of right and left boundary positions of the region of interest set by the input unit 6, for example.

Subsequently, the frequency analysis unit 44 calculates all of frequency spectra on the sound ray of the calculation echo signal received in step S10. First, the frequency analysis unit 44 sets an initial value $Z_0$ of data position "Z" (corresponding to a receiving depth) representing a series of data groups (FFT data groups) acquired for FFT calculation (step S32).

Figure 11:
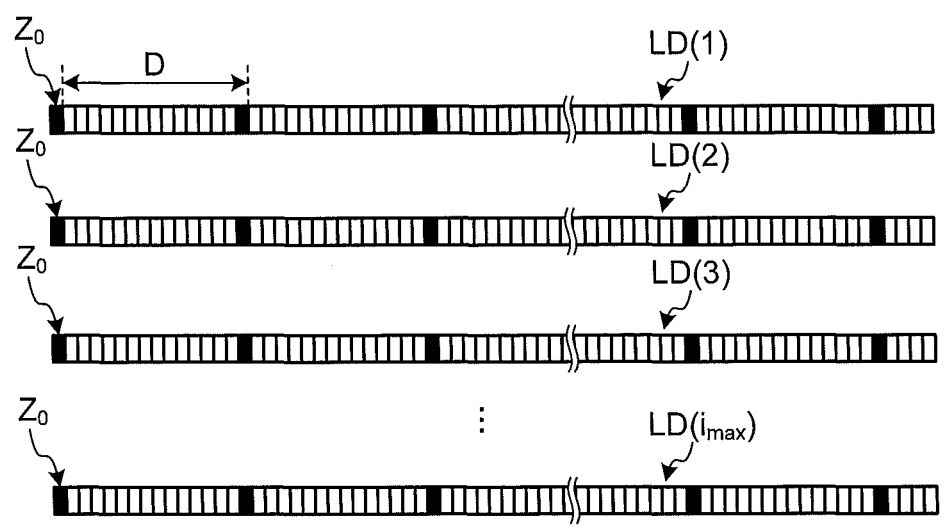
FIG. 11 is a diagram schematically illustrating a data array of a sound ray.

FIG. 11 is a diagram schematically illustrating a data array of a sound ray. In FIG. 11, a case is illustrated, in which the number of transmissions for one sound ray is $i_{max}$, the first data of the calculation echo signals LD(1) to LD($i_{max}$) corresponding to the first transmission and reception to the $i_{max}$-th transmission and reception are set as an initial values $Z_0$ of data position "Z", and the data positions are set by a step width "D". Therefore, a black area of each calculation echo signal illustrated in FIG. 11 represents the data position and the step width "D" is fifteen. A position of the initial value $Z_0$ may be arbitrarily set. For example, a data position "Z" corresponding to a top end position of the region of interest may be set as the initial value $Z_0$.

Thereafter, the frequency analysis unit 44 acquires the FFT data group at the data position "Z" (step S33). The frequency analysis unit 44 compares the data position "Z" to be acquired and a position of a focus point FP(i) of each calculation echo signal, and acquires the FFT data group at that data position "Z" by using the calculation signal having the smallest distance to the focus point. The FFT data group needs to have the number of data of the power of two. Hereinafter, the number of data of the FFT data group is assumed to be $2^n$ (where "n" is a positive integer). The number of data of the FFT data group being $2^n$ means that before the data position "Z", there are $2^{n-1}-1$ (=N) data, and after the data position "Z", there are $2^{n-1}$ (=M) data.

Figure 12:
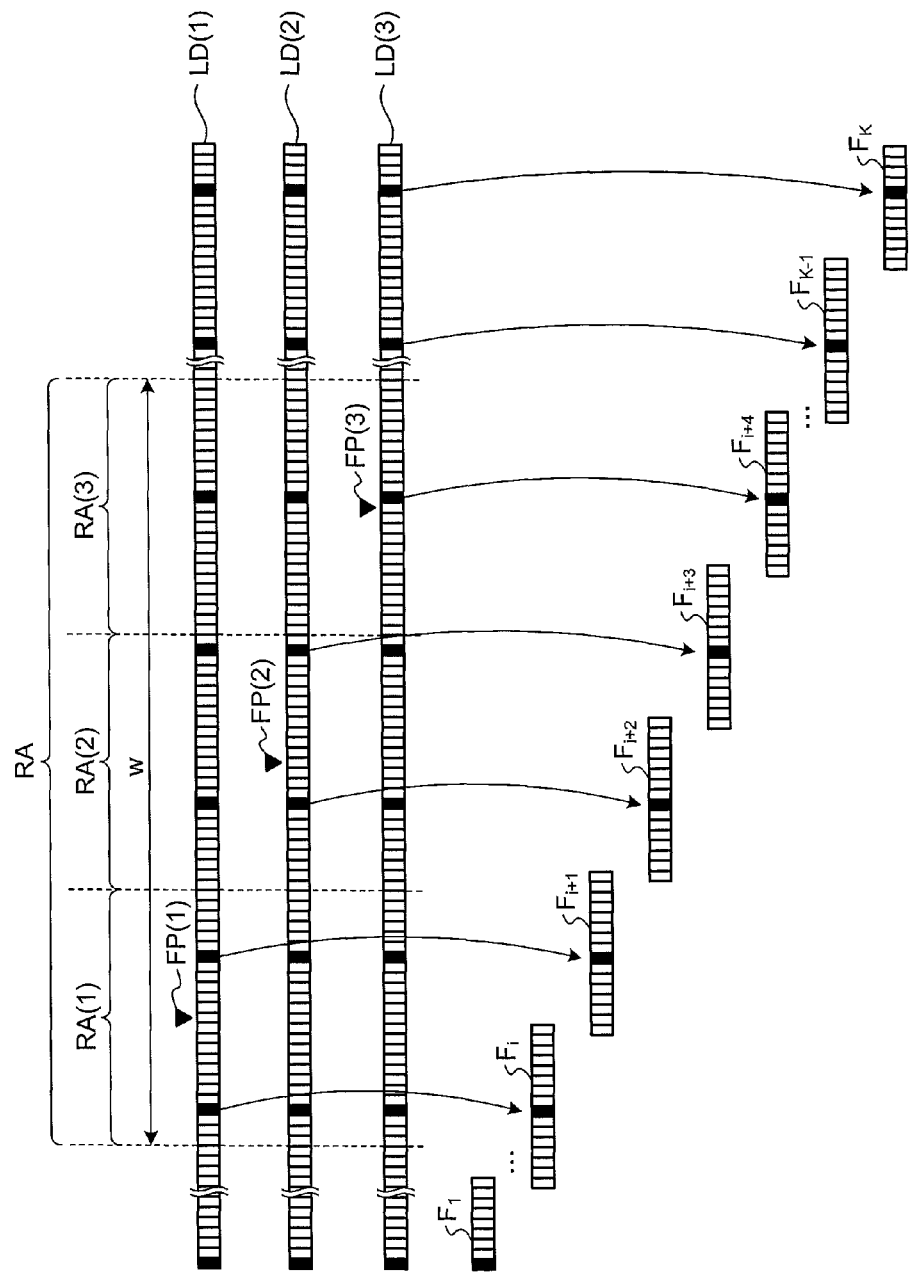
FIG. 12 is a diagram specifically illustrating an FFT data group acquiring process performed by the frequency analysis unit.

FIG. 12 is a diagram specifically illustrating the process of step S33. In FIG. 12, a case, in which the number of transmissions $i_{max}$ in one sound ray is three, is illustrated. Further, in FIG. 12, the number of data of one FFT data group is fifteen. Therefore, n=4, N=7, and M=8. Furthermore, the region of interest RA is the same as that described with reference to FIG. 8. In this case, the frequency analysis unit 44 compares the data position "Z" to be acquired with a position of a focus point of each calculation echo signal, and acquires, in the sound ray LD(1) of the first transmission and reception, FFT data groups $F_1, \ldots, F_i$, and $F_{i+1}$ (where "i" is a positive integer) at the data positions included in from the initial value $Z_0$ to the partial region of interest RA(1). Further, the frequency analysis unit 44 acquires, in the sound ray LD(2) of the second transmission and reception, FFT data groups $F_{i+2}$ and $F_{i+3}$ at the data positions included in the partial region of interest RA(2). Further, the frequency analysis unit 44 acquires, in the sound ray LD(3) of the third transmission and reception, FFT data groups $F_{i+4}, \ldots, F_{K-1}$, and $F_K$ included in from the partial region of interest RA(3) to the last data position of the sound ray LD(3).

Subsequently, the frequency analysis unit 44 applies a window function stored by the window function storage unit 83 to the acquired FFT data groups (step S34). Accordingly, by the frequency analysis unit 44 applying the window function to the acquired FFT data groups, the FFT data groups are able to be prevented from becoming discontinuous at boundaries and generation of artifacts is able to be prevented.

Thereafter, the frequency analysis unit 44 determines whether or not the FFT data group at the data position "Z" is a normal data group or not (step S35). The FFT data group being normal means that there are N data before the data position "Z" and there are M data after the data position "Z". In the case illustrated in FIG. 12, all except the FFT data groups $F_1$ and $F_K$ are normal.

As a result of the determination in step S35, if the FFT data group at the data position "Z" is normal (step S35: Yes), the frequency analysis unit 44 proceeds to later described step S37.

As a result of the determination in step S35, if the FFT data group at the data position "Z" is not normal (step S35: No), the frequency analysis unit 44 generates a normal data group by inserting zero data worth the deficit (step S36). The FFT data group determined to be not normal in step S35 has been applied with the window function before the zero data are added. Therefore, even if the zero data are inserted in the FFT data group, the data do not become discontinuous. After step S36, the frequency analysis unit 44 proceeds to later described step S37.

Figure 13:
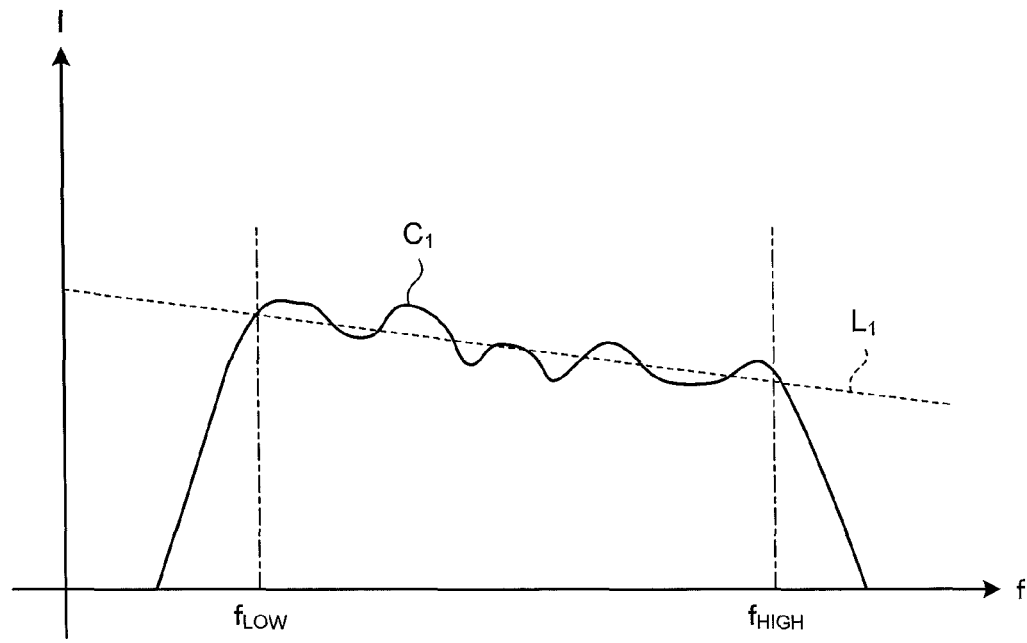
FIG. 13 is a diagram illustrating an example (first example) of a frequency spectrum calculated by the frequency analysis unit.
Figure 14:
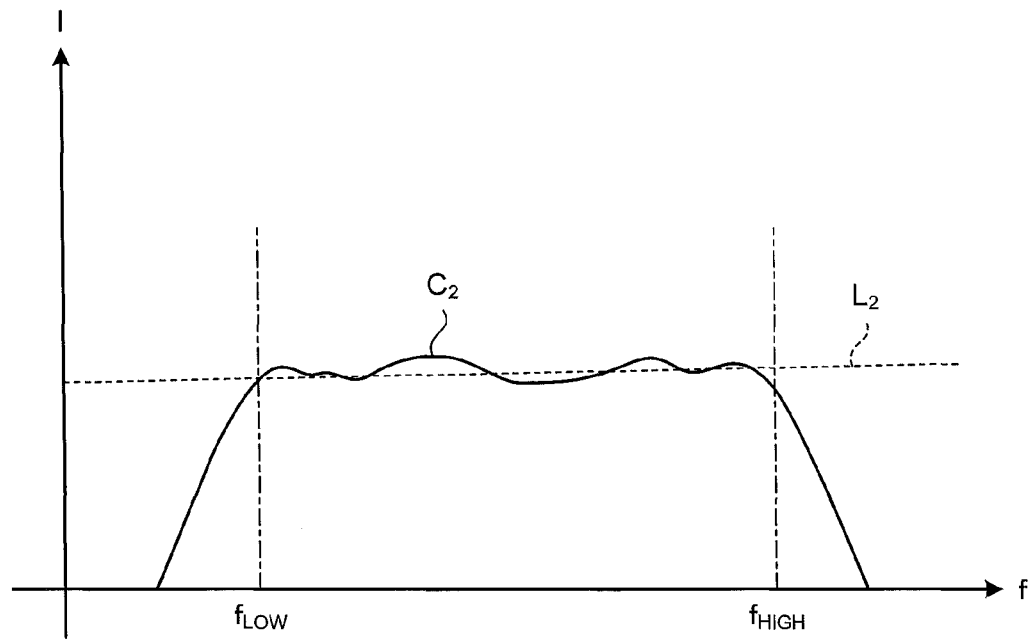
FIG. 14 is a diagram illustrating an example (second example) of the frequency spectrum calculated by the frequency analysis unit.

At step S37, the frequency analysis unit 44 acquires a frequency spectrum by performing FFT calculation using the FFT data group (step S37). FIG. 13 and FIG. 14 are diagrams illustrating examples of the frequency spectrum calculated by the frequency analysis unit 44. In FIG. 13 and FIG. 14, a horizontal axis "f" represents frequency and a vertical axis "I" represents intensity. In the frequency spectrum curves $C_1$ and $C_2$ illustrated respectively in FIG. 13 and FIG. 14, lower limit frequencies $f_{LOW}$ and upper limit frequencies $f_{HIGH}$ of the frequency spectra are parameters determined based on a frequency band of the ultrasonic probe 2, a frequency band of the pulse signal transmitted by the transmitting and receiving unit 3, and the like, and for example, $f_{LOW}$=3 MHz and $f_{HIGH}$=10 MHz. In this first embodiment, a curve and a straight line are each formed of a group of discrete points. A straight line $L_1$ illustrated in FIG. 13 and a straight line $L_2$ illustrated in FIG. 14 will be described with reference to a later described pre-correction feature data extraction process (step S12).

Subsequently, the frequency analysis unit 44 calculates a data position "Z" of an FFT data group to be next analyzed by adding the specified step width "D" to the data position "Z" (step S38). This step width "D" preferably coincides with the step width used when the B-mode image data are generated by the B-mode image data generation unit 51, but if an amount of calculation in the frequency analysis unit 44 is desired to be decreased, a value larger than the step width used by the B-mode image data generation unit 51 may be set.

Thereafter, the frequency analysis unit 44 determines whether or not the data position "Z" is greater than the last data position $Z_{max}$ (step S39). The last data position $Z_{max}$ may be a data length of the calculation echo signals LD(1) to LD(n) or a data position corresponding to a lower end of the region of interest. As a result of the determination, if the data position "Z" is larger than the last data position $Z_{max}$ (step S39: Yes), the frequency analysis unit 44 increments the sound ray number "L" by one (step S40). On the contrary, if the data position "Z" is equal to or less than the last data position $Z_{max}$ (step S39: No), the frequency analysis unit 44 returns to step S33. Accordingly, the frequency analysis unit 44 performs the FFT calculation for a total of $[\{(Z_{max}-Z_0)/D\}+1](=K)$ FFT data groups for the calculation echo signals LD(1) to LD($i_{max}$). Here, [X] represents a maximum integer not exceeding "X".

If the sound ray number "L" that has been incremented in step S40 is larger than the last sound ray number $L_{max}$ (step S41: Yes), the frequency analysis unit 44 ends the frequency analysis process. Thereafter, the ultrasonic observation apparatus 1 returns to the main routine illustrated in FIG. 5. On the contrary, if the sound ray number "L" that has been incremented in step S41 is equal to or less than the last sound ray number $L_{max}$ (step S41: No), the frequency analysis unit 44 returns to step S32.

Accordingly, the frequency analysis unit 44 performs FFT calculation "K" times for each of ($L_{max}-L_0+1$) sound rays. The last sound ray number $L_{max}$ may be given to the last sound ray received by the transmitting and receiving unit 3 or given to a sound ray corresponding to any one of left and right boundaries of the region of interest, for example. Hereinafter, the total number of FFT calculations, ($L_{max}-L_0+1$)×K, which the frequency analysis unit 44 performs on all of the sound rays is denoted by "P".

Subsequently to the frequency analysis process of the above described step S11, the feature data extracting unit 45 extracts feature data of the frequency spectrum by approximating the frequency spectrum calculated by the frequency analysis unit 44 (steps S12 and S13).

First, at step S12, the approximation unit 451 extracts pre-correction feature data by performing regression analysis, as an approximation process, on "P" frequency spectra calculated by the frequency analysis unit 44. Specifically, by calculating a linear equation for approximating a frequency spectrum in a frequency band $f_{LOW} < f < f_{HIGH}$ by regression analysis, the approximation unit 451 extracts, as the pre-correction feature data, a gradient $a_0$, an intercept $b_0$, and an intensity $c_0$ that characterize the linear equation. The straight line $L_1$ illustrated in FIG. 13 and the straight line $L_2$ illustrated in FIG. 14 are regression lines acquired by performing regression analysis respectively on the frequency spectrum curves $C_1$ and $C_2$ in this step S12.

Figure 15:
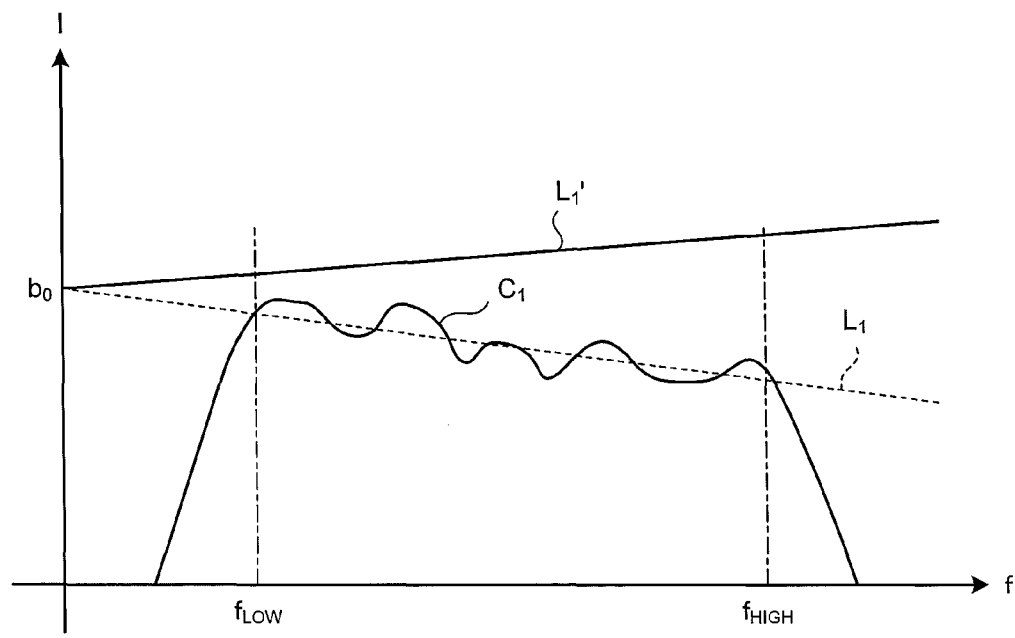
FIG. 15 is a diagram illustrating a straight line determined from feature data related to a straight line illustrated in FIG. 13, the feature data having been subjected to attenuation correction.

Thereafter, at step S13, the attenuation correction unit 452 calculates feature data by performing an attenuation correction process on the pre-correction feature data extracted by the approximation unit 451. For example, if a sampling frequency of data is 50 MHz, the sampling period is 20 (nsec). If a sound speed is 1530 (m/sec), a sampling distance interval of the data is 1530 (m/sec)×20 (nsec)/2=0.0153 (mm). If the number of data steps from the first data of the calculation echo signal LD(j) up to the data position of the FFT data group to be process is "k", that data position "Z" is 0.0153 k (mm). The attenuation correction unit 452 calculates a gradient "a", an intercept "b", and an intensity "c", which are feature data of the frequency spectrum, by substituting the value of the data position "Z" determined as described above into the receiving depth "z" of the above described equations (2) to (4). FIG. 15 is a diagram illustrating a straight line determined from feature data related to the straight line $L_1$ illustrated in FIG. 13, the feature data having been subjected to attenuation correction. An equation representing a straight line $L_1'$ illustrated in FIG. 15 is as follows.

$$I = af + b = (a_0 + 2\alpha Z)f + b_0 \quad (5)$$

As is clear from this equation (5), the straight line $L_1'$ has, as compared to the straight line $L_1$, a greater gradient and the same value of intercept.

As described above, by performing the attenuation correction by the attenuation correction unit 452, decrease in a signal intensity and darkening of an image due to influence of attenuation in a region where the receiving depth is large are able to be suppressed, and an image of a brightness uniform over the whole screen is able to be acquired.

Subsequently to step S13, the display image data generation unit 52 generates display image data, by using the B-mode image data generated by the B-mode image data generation unit 51 and the feature data calculated by the feature data extracting unit 45 (step S14).

Figure 16:
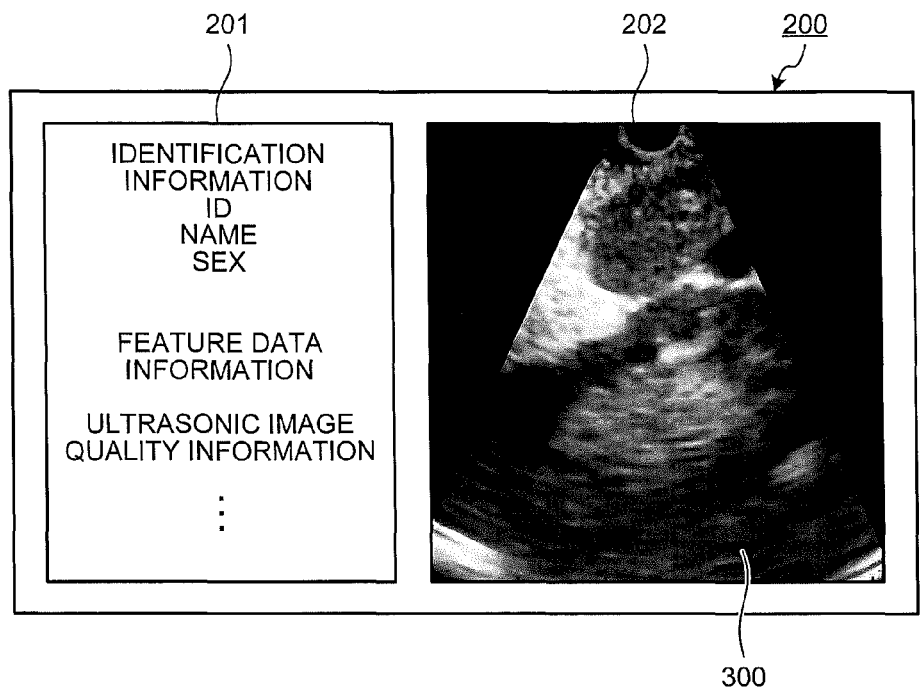
FIG. 16 is a diagram illustrating a display example (first example) of a display image in the display unit.

Thereafter, the display unit 7 displays a display image generated by the display image data generation unit 52 (step S15). FIG. 16 is a diagram illustrating a display example of a display image in the display unit 7. A display image 200 illustrated in the figure has an information display portion 201 that displays various types of information on a specimen; and an image display portion 202 that displays a tissue characterization highlighted image that highlights tissue characterization.

In the information display portion 201, for example, identification information of the specimen (ID number, name, sex, and the like), feature data information, ultrasonic image quality information such as a gain and a contrast, and the like are displayed. Display using, as feature data information, an average and a standard deviation of feature data of frequency spectra of "Q" FFT data groups positioned inside the region of interest is able to be performed. Specifically, in the information display portion, for example, "a=1.5±0.3 (dB/MHz), b=−60±2 (dB/MHz), c=−50±1.5 (dB/MHz)" may be displayed.

A tissue characterization highlighted image 300 displayed on the image display portion 202 is a gray scale image in which the feature data "b" has been uniformly allocated to red (R), green (G), and blue (B) for the B-mode image 100 illustrated in FIG. 6.

By the display unit 7 displaying the display image 200, a user of the ultrasonic observation apparatus 1 is able to more accurately grasp tissue characterization of a region of interest.

Accordingly, the ultrasonic observation apparatus 1 ends the series of processes. The ultrasonic observation apparatus 1 may periodically repeat the process of steps S1 to S15.

The tissue characterization highlighted image 300 illustrated in FIG. 16 is just an example. Instead, for example, the three feature data "a", "b", and "c" may be respectively allocated to red (R), green (G), and blue (B), to thereby display the tissue characterization highlighted image by a color image. In this case, since the tissue characterization is expressed by specific colors, the user is able to grasp the tissue characterization of the region of interest based on a color distribution of the image. Further, instead of forming the color space with the RGB color system, it may be formed by variables of a complementary color system, such as cyan, magenta, and yellow and the feature data may be allocated to each of the variables. Further, by mixing the B-mode image data and color image data in a specified ratio, the tissue characterization highlighted image data may be generated. Further, by substituting only the region of interest into color image data, the tissue characterization highlighted image data may be generated.

According to the above described first embodiment of the present invention, a plurality of focus points based on a size of a region of interest are calculated, and feature data are extracted by performing frequency analysis on an ultrasonic wave transmitted and received to and from each focus point, and thus tissue characterization is able to be accurately diagnosed and reliability of an observation result is able to be improved.

Further, according to the first embodiment, since positioning to a focus point is performed for each divided region, a phenomenon that a frequency spectrum other than the focus point is distorted due to influence of a transmission delay is able to be suppressed. Therefore, according to the first embodiment, highly accurate calculation of feature data of frequency is possible.

Further, according to the first embodiment, since B-mode image data are generated based on a signal subjected to STC correction of amplifying with an amplification factor according to a receiving depth, a frequency spectrum is calculated after performing amplification correction of offsetting influence of the STC correction and making the amplification factor constant regardless of the receiving depth, and attenuation correction is performed after this frequency spectrum is subjected to linear approximation by regression analysis, influence of attenuation associated with propagation of an ultrasonic wave is able to be removed correctly, and decrease in a frame rate of image data generated based on the received ultrasonic wave is able to be prevented.

Figure 17:
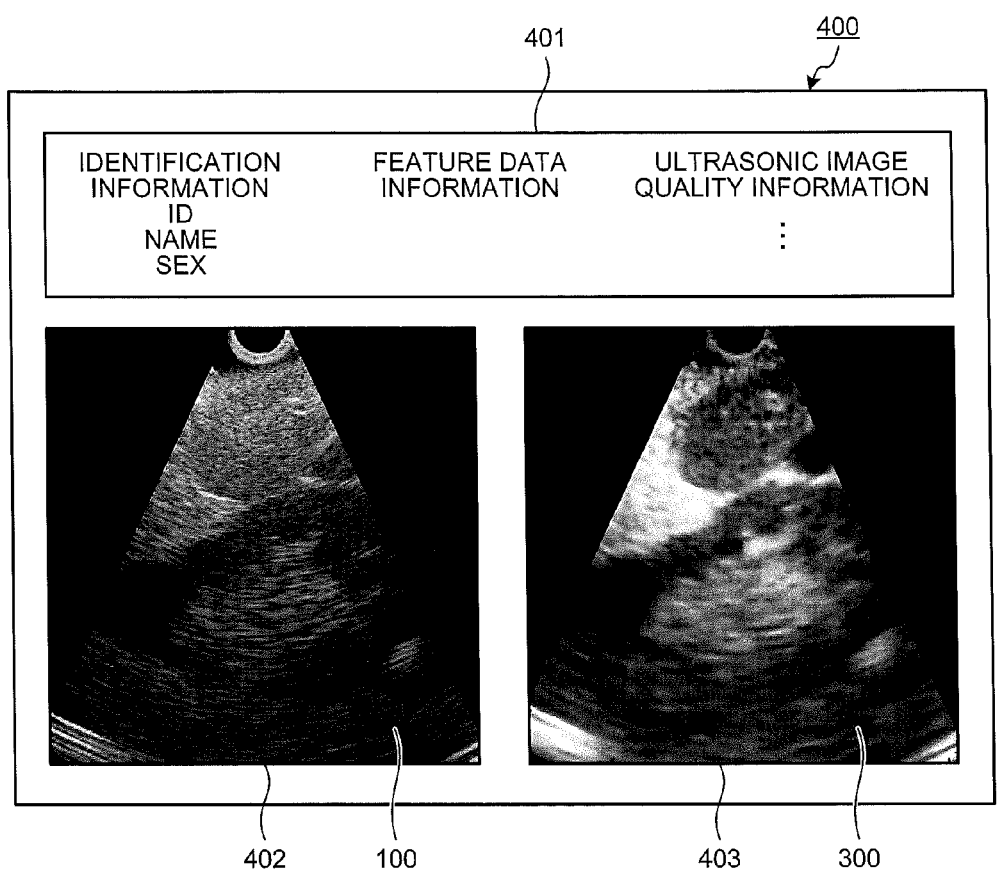
FIG. 17 is a diagram illustrating a display example (second example) of the display image in the display unit.

FIG. 17 is a diagram illustrating another display example of a display image in the display unit 7. A display image 400 illustrated in the figure has: an information display portion 401; a first image display portion 402 that displays a B-mode image; and a second image display portion 403 that displays a tissue characterization highlighted image. In the display image 400, a B-mode image 100 is displayed on the first image display portion 402 and a tissue characterization highlighted image 300 is displayed on the second image display portion 403. By displaying the B-mode image and the tissue characterization highlighted image side by side like this, differences between these images are able to be recognized on a single screen.

In the display image 400, an image displayed on the first information display portion and an image displayed on the second image display portion 403 may be able to be switched over to each other.

Further, the display of the display image 200 and the display of the display image 400 may be switched over to each other by input from the input unit 6.

Second Embodiment

In a second embodiment of the present invention, a focus point calculation process in a focus point calculation unit is different from that of the first embodiment. A configuration of an ultrasonic observation apparatus according to the second embodiment is similar to the configuration of the ultrasonic observation apparatus 1 described in the first embodiment. Thus, in the description below, to structural elements corresponding to the structural elements of the ultrasonic observation apparatus 1, the same reference signs will be appended.

Figure 18:
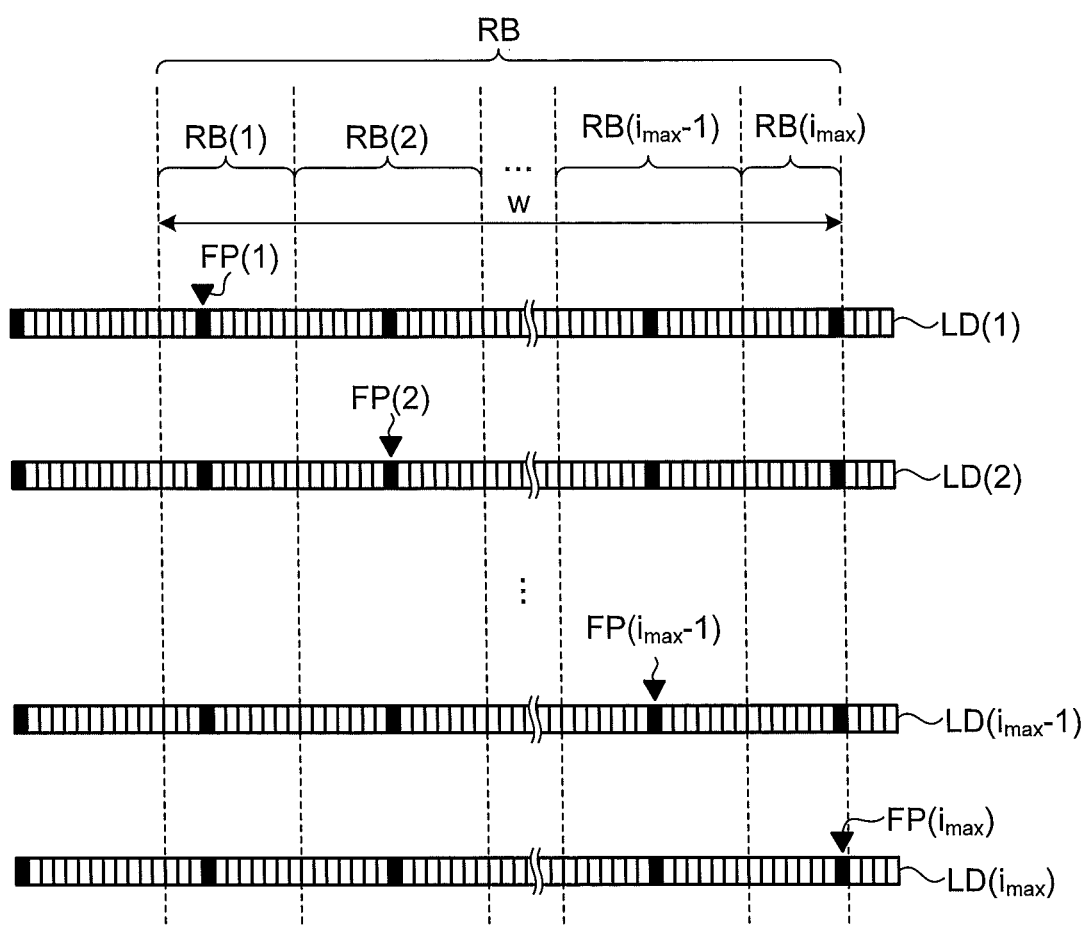
FIG. 18 is a diagram schematically illustrating an outline of a focus point calculation process performed by an ultrasonic observation apparatus according to a second embodiment of the present invention.

FIG. 18 is a diagram schematically illustrating an outline of a focus point calculation process in the second embodiment. In FIG. 18, the number of transmissions for one sound ray is $i_{max}$. Further, a region of interest RB illustrated in FIG. 18 is divided into $i_{max}$ partial regions of interest $RB(1), \ldots, RB(i_{max})$.

The focus point calculation unit 42 calculates specified data positions "Z" respectively representing a plurality of FFT data groups acquired on sound rays by the frequency analysis unit 44 as focus points $FP(j)(j=1, 2, \ldots, i_{max})$ of their corresponding partial regions of interest, and determines the number of transmissions per sound ray and a transmission timing of a calculation echo signal.

According to the above described second embodiment of the present invention, similarly to the above described first embodiment, accurate diagnosis of tissue characterization is enabled and reliability of a measurement result is able to be improved.

Further, according to the second embodiment, similarly to the above described first embodiment, by suppressing a phenomenon that a frequency spectrum other than focus points is distorted due to influence of a transmission delay, highly accurate calculation of feature data of frequency is possible.

Third Embodiment

In a third embodiment of the present invention, a focus point calculation process in a focus point calculation unit is different from that of the first embodiment. A configuration of an ultrasonic observation apparatus according to the third embodiment is similar to the configuration of the ultrasonic observation apparatus 1 described in the first embodiment. Thus, in the description below, to structural elements corresponding to the structural elements of the ultrasonic observation apparatus 1, the same reference signs will be appended.

Figure 19:
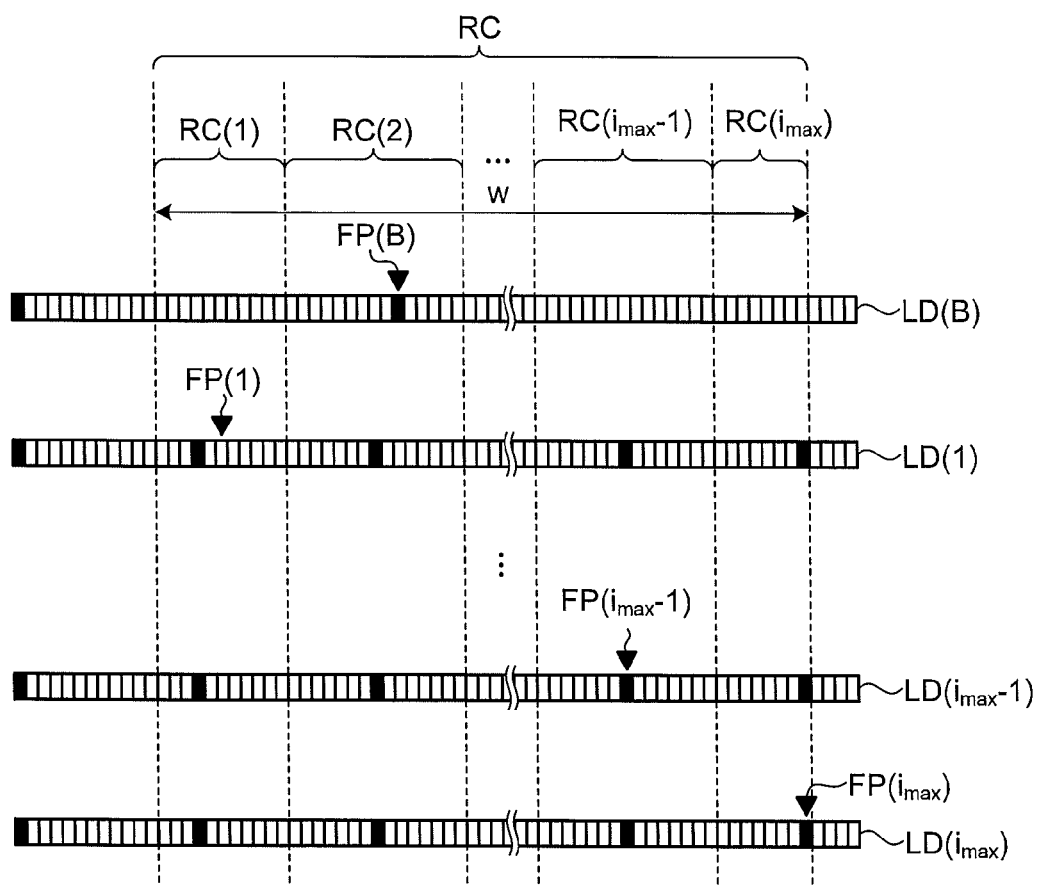
FIG. 19 is a diagram schematically illustrating an outline of a focus point calculation process performed by an ultrasonic observation apparatus according to a third embodiment of the present invention.

FIG. 19 is a diagram schematically illustrating an outline of the focus point calculation process in the third embodiment. In FIG. 19, the number of transmissions for one sound ray is $i_{max}$. Further, a region of interest RB illustrated in FIG. 19 is divided into $i_{max}$ partial regions of interest $RC(1), \ldots, RC(i_{max})$.

In the third embodiment, if a focus point of a B-mode image echo signal is included in the region of interest, the focus point calculation unit 42 does not perform setting of a focus point of a calculation echo signal for a partial region of interest including the focus point of the B-mode image echo signal. The frequency analysis unit 44 acquires, by using the B-mode image echo signal, an FFT data group in a partial region of interest for which a focus point of the calculation echo signal has not been set.

For example, in a case illustrated in FIG. 19, for a partial region of interest RC(2), a focus point FP(B) of a B-mode image echo signal LD(B) is set. Thus, for the partial region of interest RC(2), the transmitting and receiving unit 3 does not set a focus point in any of calculation echo signals LD(1) to LD($i_{max}$). The frequency analysis unit 44 acquires an FFT data group in the partial region of interest RC(2) from the B-mode image echo signal LD(B).

According to the above described third embodiment of the present invention, similarly to the above described first embodiment, accurate diagnosis of tissue characterization is enabled and reliability of a measurement result is able to be improved.

Further, according to the third embodiment, similarly to the above described first embodiment, by suppressing a phenomenon that a frequency spectrum other than focus points is distorted due to influence of a transmission delay, highly accurate calculation of feature data of frequency is possible.

Thus far, modes for carrying out the present invention have been described, but the present invention is not to be limited only by the above described first to third embodiments. For example, the number of ultrasonic transmissions per sound ray may be decreased according to calculation load situations.

Further, when the feature data of the frequency spectrum are extracted, after applying attenuation correction on the frequency spectrum calculated by the frequency analysis unit, the corrected frequency spectrum may be approximated by regression analysis.

Further, the control unit 9 may cause the amplification correction process by the amplification correction unit 43 and the attenuation correction process in the attenuation correction unit 452 to be performed collectively. This is equivalent to changing the definition of the attenuation amount "A" of the attenuation correction process in step S13 of FIG. 5 to Equation (6) below without performing the amplification correction process in step S6 of FIG. 5.

$$A' = 2\alpha z f + \gamma(z) \tag{6}$$

Here, $\gamma(z)$ on the right hand side is a difference between amplification factors $\beta$ and $\beta_0$ at the receiving depth "z" and is expressed as follows.

$$\gamma(z) = -\{(\beta_{th} - \beta_0)/z_{th}\}z + \beta_{th} - \beta_0 \; (z \leq z_{th}) \tag{7}$$

$$\gamma(z) = 0 \; (z > z_{th}) \tag{8}$$

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic observation apparatus that transmits an ultrasonic wave to a specimen and receives the ultrasonic wave reflected from the specimen, the ultrasonic observation apparatus comprising:
   a computer configured to implement:
      a region of interest setting unit configured to set information on a position, and a length in a depth direction, of a region of interest in the specimen;
      a focus point calculation unit configured to:
         divide the region of interest into a plurality of partial regions of interest according to a number of focus points in the region of interest, wherein the number of focus points is a parameter associated with the length of the region of interest set by the region of interest setting unit;
         set one or more of the number of focus points in each of the plurality of partial regions of interest; and
         determine a transmission timing according to the one or more of the number of focus points set in each of the plurality of partial regions of interest;
      a transmitting and receiving unit configured to:
         perform transmission of a number of ultrasonic waves along a sound ray in the region of interest, wherein the number of ultrasonic waves correspond to the number of focus points, and wherein the transmitted ultrasonic waves are focused on the corresponding focus point set by the focus point calculation unit; and
         receive a number of ultrasonic waves reflected from the region of interest, wherein the ultrasonic waves received from the region of interest correspond to the focus points;
      a frequency analysis unit configured to calculate frequency spectra by analyzing the ultrasonic waves received by the transmitting and receiving unit with reference to the focus points;
      a feature data extracting unit configured to extract feature data of the frequency spectra calculated by the frequency analysis unit by approximating the frequency spectra; and
      an image processing unit configured to generate display image data based on the feature data extracted by the feature data extracting unit,
   wherein the focus point calculation unit is configured to:
      set the one or more of the focus points for a B-mode image for displaying brightness converted from amplitude of the ultrasonic wave reflected from the specimen, and
      use the one or more of the focus points for the B-mode image in the partial regions of interest, and
   wherein the feature data extracting unit comprises:
      an approximation unit configured to:
         approximate the frequency spectra with a linear equation by regression analysis; and
         calculate, as pre-correction feature data for characterizing the linear equation:
            a gradient and an intercept of the linear equation, and intensity at a particular frequency within a frequency band in the frequency spectra; and
      an attenuation correction unit configured to perform an attenuation correction process on the pre-correction feature data to extract the feature data of the frequency spectra,
   wherein the frequency analysis unit is configured to calculate the frequency spectra by acquiring a data group forming a part of a data array of the ultrasonic wave received by the transmitting and receiving unit and by performing fast Fourier transform on the data group, and
   wherein the frequency analysis unit is configured to acquire a multiple data groups for the sound ray, and is configured to calculate the frequency spectra using a data group of the multiple data groups which is closest to the one or more of the focus points.

2. The ultrasonic observation apparatus according to claim 1, wherein the focus point calculation unit is configured to calculate, as the one or more of the focus points, a central position of each of the partial regions of interest in a depth direction.

3. The ultrasonic observation apparatus according to claim 1, wherein the focus point calculation unit is configured to calculate, as the one or more of the focus points, a center of the data group formed by the data array in a depth direction in each of the partial regions of interest.

4. The ultrasonic observation apparatus according to claim 1, wherein the focus point calculation unit is configured to calculate, as the one or more of the focus points, a specified position along the sound ray.

5. The ultrasonic observation apparatus according to claim 1, further comprising a display configured to display an image corresponding to the display image data generated by the image processing unit.

6. A method comprising:
   setting a position, and length in a depth direction, of a region of interest in a specimen;
   dividing the region of interest into a plurality of partial regions of interest according to a number of focus points in the region of interest, wherein the number of focus points is a parameter associated with a length of the region of interest in a depth direction, and calculating one or more of the focus points in each of the partial regions of interest;

determining a transmission timing according to the one or more of the focus points;

performing transmission of a number of ultrasonic waves along a sound ray in the region of interest,
wherein the number of ultrasonic waves correspond to the number of focus points, and
wherein the transmitted ultrasonic waves are focused on corresponding the focus point;

receiving a number of ultrasonic waves reflected from the region of interest, wherein the ultrasonic waves received from the region of interest correspond to the focus points;

calculating frequency spectra by analyzing the received ultrasonic waves with reference to the focus points;

extracting feature data of the frequency spectra by approximating the frequency spectra; and generating display image data based on the feature data, wherein the calculating of the focus point comprises:
setting the one or more of the focus points for a B-mode image for displaying brightness converted from amplitude of the ultrasonic wave reflected from the specimen; and
using the one or more of the focus points for the B-mode image in the partial regions of interest, and wherein the extracting the feature data comprises:
approximating the frequency spectra with a linear equation by regression analysis;
calculating, as pre-correction feature data for characterizing the linear equation:
a gradient and an intercept of the linear equation, and
intensity at a particular frequency within a frequency band in the frequency spectra; and
performing an attenuation correction process on the pre-correction feature data to extract the feature data of the frequency spectra, wherein calculating the frequency spectra comprises acquiring a data group forming a part of a data array of the ultrasonic wave and performing fast Fourier transform on the data group, and wherein calculating the frequency spectra further comprises acquiring a multiple data groups for the sound ray, and calculating the frequency spectra using a data group of the multiple data groups which is closest to the one or more of the focus points.

7. A non-transitory computer readable recording medium having an executable program recorded thereon, the program instructing a processor to execute:
setting a position, and length in a depth direction, of a region of interest in the specimen;
dividing the region of interest into a plurality of partial regions of interest according to the number of focus points in the region of interest, the number of focus points being a parameter associated with a length of the region of interest in a depth direction, and calculating one or more of the focus points in each of the partial regions of interest;

determining a transmission timing according to the one or more of the focus points;

performing transmission of a number of ultrasonic waves along a sound ray in the region of interest,
wherein the number of ultrasonic waves correspond to the number of focus points, and
wherein the transmitted ultrasonic waves are focused on corresponding the focus point;

receiving a number of ultrasonic waves reflected from the region of interest, wherein the ultrasonic waves received from the region of interest corresponds to the focus points;

calculating frequency spectra by analyzing the received ultrasonic waves with reference to the focus points;

extracting feature data of the frequency spectra by approximating the frequency spectra; and generating display image data based on the feature data, wherein the calculating of the focus point comprises:
setting the one or more of the focus points for a B-mode image for displaying brightness converted from amplitude of the ultrasonic wave reflected from the specimen; and
using the one or more of the focus points for the B-mode image in the partial regions of interest, and wherein the extracting the feature data comprises:
approximating the frequency spectra with a linear equation by regression analysis;
calculating, as pre-correction feature data for characterizing the linear equation:
a gradient and an intercept of the linear equation, and
intensity at a particular frequency within a frequency band in the frequency spectra; and performing an attenuation correction process on the pre-correction feature data to extract the feature data of the frequency spectra, wherein calculating the frequency spectra comprises acquiring a data group forming a part of a data array of the ultrasonic wave and performing fast Fourier transform on the data group, and wherein calculating the frequency spectra further comprises acquiring a multiple data groups for the sound ray, and calculating the frequency spectra using a data group of the multiple data groups which is closest to the one or more of the focus points.

* * * * *